US006683112B2

(12) United States Patent
Chen et al.

(10) Patent No.: US 6,683,112 B2
(45) Date of Patent: Jan. 27, 2004

(54) GABAPENTIN PRODRUGS AND FORMULATIONS

(75) Inventors: Chih-Ming Chen, Davie, FL (US); Jane Chen, Davie, FL (US)

(73) Assignee: Andrx Corporation, Davie, FL (US)

( * ) Notice: Subject to any disclaimer, the term of this patent is extended or adjusted under 35 U.S.C. 154(b) by 36 days.

(21) Appl. No.: 10/040,251

(22) Filed: Oct. 23, 2001

(65) Prior Publication Data

US 2002/0107208 A1 Aug. 8, 2002

Related U.S. Application Data

(60) Provisional application No. 60/242,924, filed on Oct. 24, 2000.

(51) Int. Cl.[7] ......................... A01N 37/12; A01N 43/38; C07C 229/00; C07C 69/96
(52) U.S. Cl. ......................... 514/561; 514/420; 514/423; 514/512; 514/557; 558/275; 558/276; 558/277; 562/507
(58) Field of Search ................................. 514/420, 423, 514/512, 557, 561; 558/276, 275, 277; 562/507

(56) References Cited

U.S. PATENT DOCUMENTS

| 4,087,544 | A | * | 5/1978 | Satzinger et al. |
| 4,612,008 | A | * | 9/1986 | Wong et al. |
| 4,851,426 | A | * | 7/1989 | Ladkani et al. |
| 5,837,379 | A | * | 11/1998 | Chen et al. |
| 6,103,932 | A | * | 8/2000 | Horwell et al. |

\* cited by examiner

Primary Examiner—James O. Wilson
Assistant Examiner—Traviss C. McIntosh, III
(74) Attorney, Agent, or Firm—Davidson, Davidson & Kappel, LLC

(57) ABSTRACT

The present invention relates to novel prodrugs of gabapentin and to pharmaceutical formulations and sustained release formulations containing the prodrugs.

10 Claims, No Drawings

GABAPENTIN PRODRUGS AND FORMULATIONS

This application claims priority to provisional application No. 60/242,924 filed Oct. 24, 2000, the disclosure of which is hereby incorporated by reference.

BACKGROUND OF THE INVENTION

Gabapentin is a cyclohexaneacetic acid derivative that is sold under the trademark NEURONTIN for the treatment of partial seizures in adults with epilepsy. The current administration regimen requires 900 to 1800 mgs/day and given in divided doses of three times per day using 300–400 mg capsules. While the drug is highly effective for its prescribed use, there is a need to develop a version of the drug that is administered in a once-a-day regimen and which provides an equally efficacious pharmaceutical product and improved side effect profile.

Gabapentin is 1-(aminomethyl)cyclohexaneacetic acid. This compound is highly soluble in water and in both basic and acidic conditions. The drug per se is not extensively metabolized in humans and is eliminated via renal excretion essentially unchanged. At the typical dosage range (300–600 mgs T.I.D.) the oral bioavailability is approximately sixty percent. The gabapentin elimination half life is five to seven hours and is unaltered by dose or following multiple dosing. Thus, there is a need for an improved product profile that increases bioavailability and provides for a once a day dosing regimen. U.S. Pat. No. 4,087,544 discloses the compound known as gabapentin and various analogs thereof including, for example, the alkyl esters having an R group in place of the carboxylic acid hydrogen wherein R is selected from an alkyl radical containing up to 8 carbon atoms. Specific alkyl groups disclosed include ethyl, methyl and n-butyl. Pharmaceutical compositions and methods of use are also generically disclosed. There is no teaching of therein or reference to the use of any of these compounds in a sustained release formulation. U.S. Pat. No. 5,955,103 discloses certain dosage forms that may contain various active ingredients including gabapentin but it does not disclose or relate to sustained release dosage forms containing pro-drugs of gabapentin. There is a need to combine the advantages of a prodrug of gabapentin and a sustained release delivery system to provide the slow and efficacious delivery of the pro-drug and ultimately the active metabolite of said prodrug-gabapentin.

U.S. Pat. No. 4,595,695 discloses certain prodrugs of valproic acid and describes, for example, the 1'ethoxycarbonyloxyethyl ester of valproic acid. This patent does not disclose or describe gabapentin.

SUMMARY OF THE INVENTION

The present invention comprises a prodrug of gabapentin having the formula:

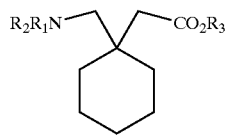

(I)

and the pharmaceutically acceptable salts thereof wherein:
R1 and R2 are independently selected from hydrogen and C1–C6alkyl, C2–C6alkenyl, C2–C6alkynyl and substituted versions thereof wherein the substituents are selected from halogen, C1–C6alkyl, hydroxy, alkoxy or carboxy; and R3 is a variable having the formula —(R4)—O—(CO)—O—R5 wherein R4 is selected from C1–C6alkyl, C2–C6alkenyl, C2–C6alkynyl and substituted versions thereof and R5 is selected from C1–C6alkyl, C2–C6alkenyl or C2–C6alkynyl and substituted versions thereof wherein the substituents are selected from C1–C6alkyl, halogen, hydroxy, alkoxy or carboxy.

Alternatively, R3 is selected from C1–C6 alkyl, alkenyl and alkynyl groups or sugars selected from chiral sugars or racemic mixtures and, while certain compounds in this category are not novel per se, the sustained release dosage forms having a compound of formula I wherein R3 is as above are novel and are part of the claimed invention herein. The preferred alkyl group is selected from an ethyl group. Other viable candidates include methyl, propyl, butyl, isobutyl, pentyl, hexyl and other isomers of the alkyl groups and substituted versions thereof wherein the substituents are selected from —NR1R2, halogen, hydroxy, and alkoxy. For example, R3 is selected from 1-(3-propylamine) or —CH2—CH2—CH2NH2.

In certain embodiments, the present invention is directed to a compound having the formula (I):

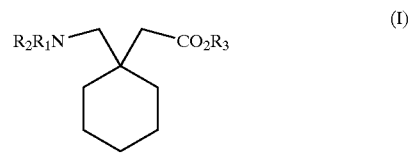

(I)

and the pharmaceutically acceptable salts thereof wherein:
R1 and R2 are independently selected from hydrogen, t-butyloxycarbonyl and C1–C6 alkyl, C2–C6alkenyl, C2–C6alkynyl and substituted versions thereof wherein the substituents are selected from halogen C1–C6alkyl, hydroxy,alkoxy, or carboxy;

and R3 is a variable having the formula —(R4)—O—(CO)—O—R5 wherein R4 is selected from C1–C6alkyl, C2–C6alkenyl, C2–C6alkynyl and substituted versions thereof and R5 is selected from C1–C6alkyl, C2–C6alkenyl or C2–C6alkynyl and substituted versions thereof wherein the substituents are selected from C1–C6alkyl, halogen, hydroxy, alkoxy or carboxy; or R3 is selected from C1–C6 alkenyl and alkynyl groups or sugars selected from chiral sugars or racemic mixtures thereof and substituted versions thereof wherein the substituents are selected from —NR1R2, halogen, hydroxy, and alkoxy or R3 is selected from substituted C1–C6alkyl wherein the substituents are selected from —NR1R2, halogen, hydroxy, and alkoxy.

In certain embodiments, the present invention is further directed to a sustained release formulation comprising a compound of formula I wherein R3 is selected from C1–C6 alkyl and substituted versions thereof wherein the substituents are selected from —NR1R2, halogen, hydroxy, and alkoxy and a pharmaceutically acceptable excipient wherein at least one of said excipients provides a sustained release profile relative to the immediate release form of gabapentin or gabapentin analog.

In a preferred embodiment, R1 and R2 are selected from hydrogen; R4 is selected from methylene —(CH—) substituted with CH3 and R5 is selected from C2H5. Thus, the preferred prodrug is the 1'ethoxycarbonyloxyethyl ester of gabapentin and the pharmaceutically acceptable salts thereof or a compound of formula II:

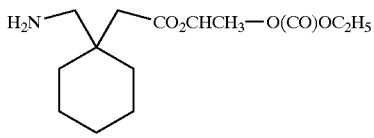
(II)

The present invention also relates to the single enantiomers or diasteroisomers of the prodrugs of formula I when a chiral center or centers is present on the molecule and to pharmaceutical compositions and dosage forms containing such enantiomers or diastereomers. In particular, it is believed that when R3 is a chiral sugar moiety, the different chiral molecules will have different rates of cleavage and metabolism and could provide both immediate release of and sustained release of the cleaved achiral gabapentin molecule.

The present invention further comprises pharmaceutical compositions comprising a compound of formula I or II with the variables described above and a pharmaceutically acceptable excipient.

The present invention also comprises a method of treating patients having seizures comprising administering a pharmaceutically effective amount of a prodrug of formula I or II or a pharmaceutical composition thereof to said patient.

The present invention comprises a dosage form having a compound of formula I or II as the penultimate active ingredient (Prodrug) in the dosage form wherein the compound of formula I or II is converted or metabolized in vivo to gabapentin or a pharmaceutically acceptable salt thereof.

The present invention also comprises a sustained release formulation and dosage form comprising a compound of formula I or II and pharmaceutically acceptable excipients that provide a controlled release of the prodrug and the sustained delivery of the metabolite gabapentin or a salt thereof.

The present invention also relates to a sustained release rate and delivery profile in vitro or in vivo and in the gastric system and in the blood plasma of a patient treated with the prodrug of formula I or II relative to the release rate and delivery profile of gabapentin.

DETAILED DESCRIPTION OF THE INVENTION

The present invention relates to novel and useful prodrugs of gabapentin, processes to produce such prodrugs and products produced by the processes. In addition, the present invention relates to use of the prodrugs herein as dosage form ingredients to produce, upon ingestion, pharmaceutically active gabapentin as a metabolic product of the gabapentin prodrug of formula I and II and their pharmaceutically acceptable salts. In addition, the invention relates to the single enantiomers or diasteromers of the prodrugs of the invention. Either or both enantiomers may undergo different rates of enzymatic hydrolysis and thus are both useful in their own right. The novel esters act as a prodrug that exhibits characteristics of a slow release profile of the parent drug. In addition, the prodrug can be formulated into pharmaceutical dosage forms including sustained release dosage forms to produce a slow release product. The slow release occurs from the continual metabolism of the prodrug to the active gabapentin and from the properties of the dosage form that can be manipulated and adjusted to provide slow release profiles that are beneficial to the patient from a compliance perspective and from an efficacy and side effect perspective. The particularly preferred prodrugs are selected from compounds of formula I as recited above and more particularly from a compound of formula II and their pharmaceutically acceptable salts.

A compound of formula I and formula II are readily made from commercially available gabapentin or a salt or derivative thereof. In a preferred process and in order to prevent lactam formation during modification and esterification of the gabepentin precursor (the carboxylic acid), the preferred precursor is the amine salt of gabapentin. This precursor is unlikely to form or cannot form the lactam because of the temporary loss of the nucleophilc electrons on the free amine of gabapentin. The 1'ethoxycarbonyloxyethyl ester prodrug of gabapentin is particularly believed to be an excellent precursor and prodrug because the metabolic pathway of this compound will yield biologically harmless or neutral metabolic components as well as the active gabapentin. This ester has been used in other active ingredients including valproic acid and alpha-aminopenicillins and penicillin G. It has been found that absorption of such esters from the intestinal tract is superior to the absorption of the free acids which will yield higher blood levels of the drug. In addition to having higher blood levels, it is believed that the particular combination of higher blood levels as well as the properties of a dosage form, in particular a sustained release dosage form, provide the most beneficial range of properties. Thus, in a preferred embodiment, the combination or synergistic combination of the prodrugs of the invention and the sustained release excipients and forms of the invention create the most ideal profile for the administration of gabapentin and represent a significant advance over the immediate release form of the drug. Oral dosage forms are preferred.

The invention also relates to a process for producing such drugs. In particular, compounds of formula I may be prepared by reacting a compound of formula III with a compound of formula IV to form a compound of formula I (see Scheme I).

X represents a halogen atom (Cl, Br, F or I) and, in the case of the preferred embodiment, the material can be obtained according to the procedure described in U.S. Pat. No. 4,595,695. Y is the metal salt of the carboxylic acid. A compound of formula IV can also be made by an analogous procedure to that described for the compound disclosed in U.S. Pat. No. 4,595,695 and is typically used in at least a one molar ratio. The conditions of the reaction can, of course, be modifed for the particular ester or

SCHEME 1

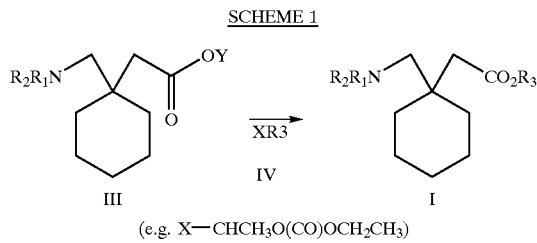

(e.g. X—CHCH₃O(CO)OCH₂CH₃)

prodrug that is desired.

Thus, the invention comprises a process comprising:
(1) reacting a compound of formula III with
(2) a compound of formula IV to form a compound of formula I. Alternatively, the compounds of the invention are made according to the process described in Scheme 2 below.

In Scheme 2, the process comprises the steps of:
(a) adding gabapentin or a derivative thereof to a bead to form a carboxylic acid reactive component;

(b) reacting the carboyxlic acid component with acid or base to form a reactive species;
(c) reacting the reactive species formed in step b with an esterfying component to form, upon esterification, a compound of formula I or a salt thereof.

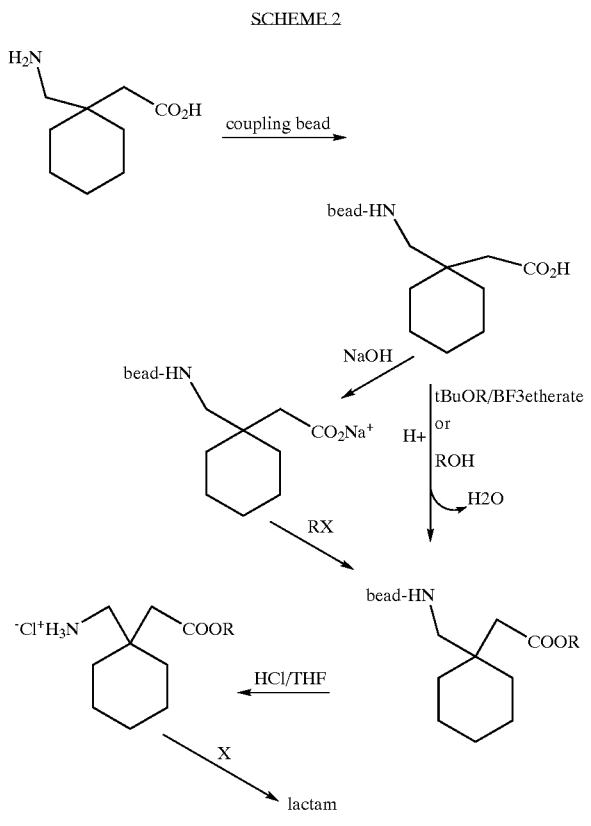

In this process, a support is used to hold the amine portion of the gabapentin and the carboxylic acid moiety can then be modified as desired to form compounds of formula I or II without the presence of the undesired lactam. As shown above, the prodrugs can be made under basic or acidic conditions to form the prodrug salt that may be used in pure form as the "active ingredient" in the drug tablet. This "active ingredient" then converts to gabapentin upon administration in oral form to the patient in need of treatment thereof. It is preferred and necessary that aprotic solvents are used in ester formation in order to prevent hydrolysis of the ester back to starting material(s). Similarly and not shown in a scheme, the amine group may be modified to alkylated derivatives thereof by standard organic reactions (amine alkylation using RX and amine) to form NR1H or NR1R2 wherein R1 and R2 are selected from alkyl, alkenyl and alkynyl moieties. These groups may be added before or after esterification to form the prodrug from the gabapentin precursor.

The preferred synthetic route to form, for example, the ethyl ester of gabapentin as the hydrochloride salt (Ethyl 1-aminomethyl-1-cyclohexane-acetate hydrochloride salt) is prepared using thionyl chloride ($SOCl_2$ in ethanol). The preferred synthetic route to the synthesis of [(Ethoxycarbonyl)oxy]ethyl gabapentin ester hydrochloride (the hydrochloride salt of a compound of formula II) involves (1) protecting the nitrogen with boc (using boc-anhydride); (2) treating the N-boc-gabapentin with tetrabutyl ammonium hydrogen sulfate and 2M sodium hydroxide to generate an activiated N-tetrabutylsalt that (3) reacts with ethoxycarbonyloxyethylchloride to form the boc protected ethoxycarbonyloxyethyl gabapentin that is (4) treated with hydrochloric acid to form the compound of formula II (as the HCl salt). The ethoxycarbonyloxyethylchloride was prepared from 1-chloroethylchloroformate and ethanol using pyridine and methylene chloride as the solvent system (see Scheme III).

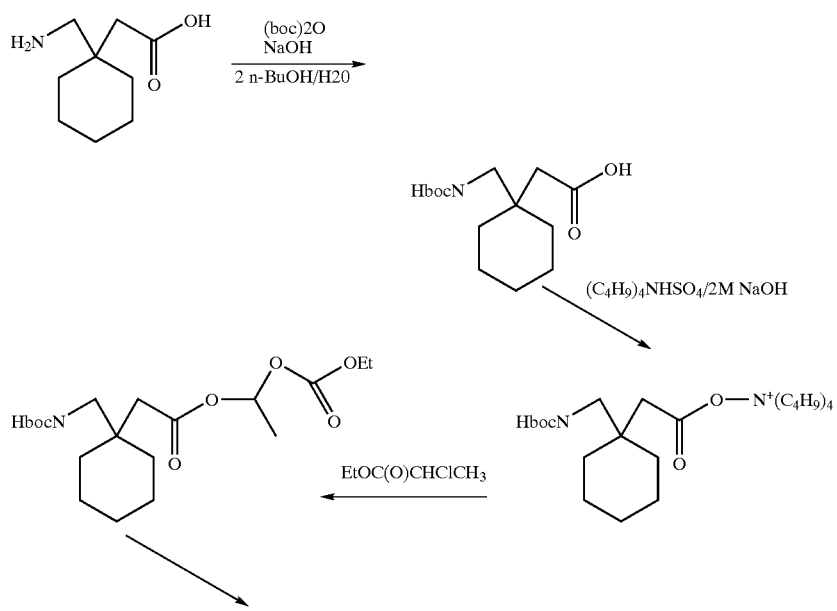

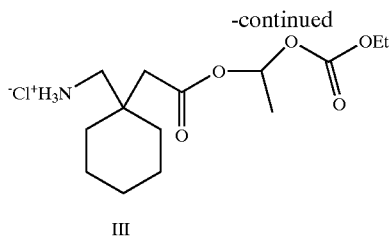

III

Pharmaceutical Compositions

Compounds of the invention are then added to pharmaceutically acceptable excipients to form pharmaceutical compositions. The invention comprises a pharmaceutical composition comprising the prodrug of formula I or II and a pharmaceutically acceptable excipients. These excipients are typically selected from the class of inactive reagents used in the pharmaceutical formulation arts and include any pharmaceutically acceptable polymer or excipient such as sucrose, lactose and the like. Typical excipients include binders, disintegrants, lubricants, surfactants, wetting agents, swellable polymers, coating ingredients for films or sustained release or immediate release coatings, fillers, water absorbing materials, hardening agents, formulating agents and processing aids. The drug can be as drug per se in any particle size as well as in the form of a granule or as a coating on a bead or sphere.

On oral administration of the prodrug or a pharmaceutical formulation thereof, it is believed that the ester is easily absorbed from the digestive tract and through enzymatic hydrolysis would liberate the active ingredient gabapentin as the prodrug is exposed to a hydrolytic environment. It is also believed that the esters of the invention are somewhat resistant to non-enzymatic hydrolysis and would thus be stable in the gut prior to absorbtion through the digestive tract. Stability studies of the prodrug in vitro will demonstrate that the prodrug converts to gabapentin. These stability studies are conducted at room temperature and may be conducted in blood plasma. Of course, the stability of the prodrug is increased when it is converted to a salt form such as the hydrochloride salt. Exposure to hydrolytic enzymes in vitro as well as in vivo releases gabapentin.

Pharmaceutical Dosage Forms

Standard dosage forms may incorporate the prodrugs of this invention to form, in a preferred embodiment, oral dosage forms. Oral dosage forms represent the majority of pharmaceutical dosage forms and are the form most preferred by patients for chronic administration or acute administration of medicaments. Pharmaceutical capsules or tablets may be prepared and which comprise the prodrug and inactive ingredients such as lactose or other sugar, corn starch and talc. Other inactive ingredients can include gelatin, titanium dioxide and yellow iron oxide. The ingredients are dry mixed and compressed into tablets or are mixed and inserted into capsules. Color coatings may be applied to the tablet.

The most preferred pharmaceutical dosage forms include controlled delivery systems containing the prodrug of formula I or II. In one embodiment, the controlled delivery system may be an osmotic system such as that described in U.S. Pat. No. 4,612,008 which is hereby incorporated by reference. This patent describes a push-pull osmotic pump system that comprises (a) a semipermeable membrane; (b) a compartment; (c) a first composition or layer having drug, osmagent and osmopolymer; (d) a second composition or layer having osmagent and osmopolymer and (e) a passageway connecting the first drug containing composition to the exterior of the device to permit release of the drug. Alternatively, the prodrug of the invention may be added to a controlled delivery device such as a single composition or single layer system having a membrane; a compartment having an osmopolymer and an osmagent and drug wherein the membrane has an enteric coated polymer. Such a system is described in, for example, U.S. Pat. No. 5,837,379 which is hereby incorporated by reference. The single composition systems and the bilayer (or trilayer) osmotic push pull systems are suitable for both water soluble and for water insoluble drugs. Thus, in its broadest form for osmotic systems, the present invention comprises a sustained release dosage form, comprising (1) a core having (a) a prodrug of formula I and (b) at least one osmotically effective component that is selected from the prodrug itself, an osmagent and an osmopolymer; (2) a membrane surrounding the core and, optionally, (3) at least one passageway wherein the passageway is formed in vitro or in vivo or both.

Osmagents are typically selected from, for example, water soluble inorganic or organic small molecules such as sodium chloride or lactose or the like. Osmopolymers are generally selected from water swellable polymers such as a hydrogel and specifically include, for example, polyethylene oxides and the like. Osmagents and osmopolymers are more particularly described in the '008 patent incorporated by reference above and all may be incorporate into the recited dosage form.

In the single layer or single composition sytems, the dosage forms may be formed by forming granulations of the prodrug along with other excipients to form a granule that is further blended with, for example, a lubricant and compressed into a tablet. The tablet is seal coated with, for example, a coating of hydroxypropyl methyl cellulose (Opadry Clear or Yellow) or an alternative coating of, for example PVP. An enteric coating may optionally be applied to the tablet and an SR coating is also applied to the tablet to form a sustained release delivery device. Optional cosmetic or color coatings may be added as the last film layer of the tablet and holes may or may not be drilled into the core or the external tablet. Alternatively, the prodrug may be mixed with all the excipients including, for example, osmopolymer such as polyox, osmagent such as lactose along with optional excipients such as fillers, binders, lubricants and/or disintegrants to form a blend that is compressed to a tablet, coated with Opadry clear or equivalent film, optionally enteric coated and then SR coated to form a controlled release device.

Other suitable sustained release dosage forms include hydrogel or matrix systems that permit slow release of the drug or drug/polymer. One hundred percent of the drug is released over a twenty-four hour period. 0–20% of the drug is released in the first four hours while the remaining 80% is released over the next twenty hours. The dosage forms may be in the form of pellets or beads that are "active pellets" either as the drug granule or as active ingredient coated on a neutral core to form an active granule or bead that is further coated with a coating that provides slow release of the drug-for example, Eudragit® or ethylcellulose.

It is also envisioned that the slow release prodrug or formulations of the invention can, in some cases, be combined with other active ingredients including immediate release gabapentin or other anti-epileptic drugs to provide combination products.

What is claimed is:

1. A compound having the formula (I):

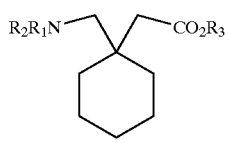

(I)

and the pharmaceutically acceptable salts thereof wherein:
R1 and R2 are independently selected from the group consisting of hydrogen, t-butyloxycarbonyl and C1–C6 alkyl, C2–C6alkenyl, C2–C6alkynyl and substituted versions thereof wherein the substituents are selected from halogen, C1–C6alkyl, hydroxy, alkoxy, and carboxy;
and R3 is a variable having the formula —(R4)—O—(CO)—O—R5 wherein R4 is selected from C1–C6alkyl, C2–C6alkenyl, C2–C6alkynyl and substituted versions thereof and R5 is selected from the group consisting of C1–C6alkyl, C2–C6alkenyl and C2–C6alkynyl and substituted versions thereof wherein the substituents are selected from the group consisting of C1–C6alkyl, halogen, hydroxy, alkoxy and carboxy; or R3 is selected from C2–C6 alkenyl and alkoxy groups or sugars selected from chiral sugars or racemic mixtures thereof and substituted versions thereof wherein the substituents are selected from —NR1R2, halogen, hydroxy, and alkoxy or R3 is selected from substituted C1–C6alkyl wherein the substituents are selected from —NR1R2, halogen, hydroxy, and alkoxy.

2. A compound according to claim 1 wherein R4 is selected from —(CH—) substituted with CH3 and R5 is selected from C2H5.

3. A compound according to claim 1 and the pharmaceutically acceptable salts thereof of formula II:

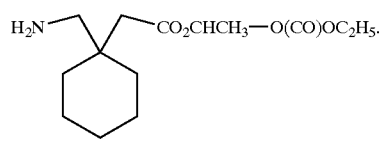

(II)

4. A compound according to claim 1 wherein the compound is a single enantiomer or diastereomer.

5. A pharmaceutical composition comprising a compound according to claim 1 and a pharmaceutically acceptable excipient.

6. A sustained release formulation comprising a compound of formula I according to claim 1 wherein R3 is selected from substituted C1–C6 alkyl wherin the substituents are selected from —NR1R2, halogen, hydroxy, and alkoxy and a pharmaceutically acceptable excipient wherein at least one of said excipients provides a sustained release profile relative to the immediate release form of gabapentin or gabapentin analog.

7. A method of treating patients prone to seizures comprising administering a pharmaceutically effective amount of formula I or a pharmaceutical composition thereof according to claim 1 to said patient.

8. A dosage form having a compound of formula I according to claim 1 as the penultimate ingredient in the dosage form wherein the compound of formula I is converted or metabolized in vivo to gabapentin or a pharmaceutically acceptable salt thereof.

9. A sustained release formulation and dosage form comprising a compound of formula I according to claim 1 and pharmaceutically acceptable excipients that provide a controlled release of the prodrug and the sustained delivery of the metabolite gabapentin or a salt thereof.

10. A sustained release dosage form having a sustained release rate and delivery profile in vitro or in vivo and in the gastric system and in the blood plasma of a patient with the prodrug of formula I according to claim 1 relative to the release rate and delivery profile of gabapentin.

* * * * *